United States Patent [19]

Jekkel et al.

[11] Patent Number: 5,403,728
[45] Date of Patent: Apr. 4, 1995

[54] MICROBIAL PROCESS FOR PREPARING MEVINOLIN BY A STRAIN OF ASPERGILLUS

[75] Inventors: Antónia Jekkel; Éva Ilkőy; István M. Szabó; Gábor Ambrus; Attila Andor; Ilona Varga; Imre Moravcsik, all of Budapest; István Szabó, Kecskemét; János Erdei, Debrecen; Kálmán Pólya, Debrecen; András Kiss, Debrecen; László Cséke, Debrecen; Károly Nagy, Debrecen; Mihály Kaszás, Debrecen; Lajos Kiss, Debrecen; István Magyi, Debrecen; Edit Halász, Debrecen; György Sántha, Debrecen, all of Hungary

[73] Assignee: BIOGAL Gyogyszergyar RT, Debrecen, Hungary

[21] Appl. No.: 77,364

[22] Filed: Jun. 17, 1993

[30] Foreign Application Priority Data

Jun. 17, 1992 [HU] Hungary .......................... P9202020

[51] Int. Cl.⁶ ...................... C12P 17/06; C12P 7/00; C12P 7/02
[52] U.S. Cl. .................................. 435/125; 435/123; 435/127; 435/132; 435/171; 435/256.1
[58] Field of Search .................. 435/123, 256.1, 125, 435/127, 171, 132

[56] References Cited

U.S. PATENT DOCUMENTS

| | | | |
|---|---|---|---|
| 4,231,938 | 11/1980 | Monaghan | 435/125 |
| 4,319,039 | 3/1982 | AlbersSchmberg | 435/125 |
| 5,153,124 | 10/1992 | Furuya | 435/125 |

*Primary Examiner*—Marian Knode
*Attorney, Agent, or Firm*—Keil & Weinkauf

[57] ABSTRACT

The invention refers to a new microbial process for preparing β,δ-dihydroxy-7-[1,2,6,7,8,8a-hexahydro-2.6-dimethyl-8-(2-methyl-butyryloxy)-naphthalen-1-yl]-heptanoic acid δ-lactone of formula (I) and β,δ-dihydroxy-7-[1,2,6,7,8,8a-hexahydro-2.6-dimethyl-8-(2-methylbutyryloxy)-naphtalen-1-yl]-heptanoic acid of formula (II),

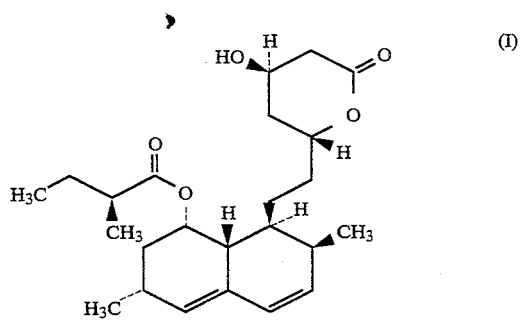

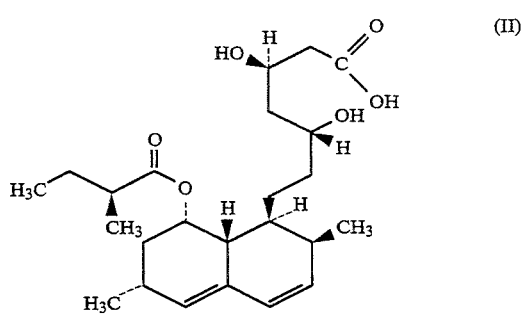

by the aerobic fermentation of the submerged culture of an imperfect fungus strain biosynthesizing the above compounds, in a nutrient medium containing utilizable carbon and nitrogen sources as well as mineral salts, and by isolating the product of formula (I), which comprises cultivating a strain of the new *Aspergillus obscurus* fungus species producing the above compound(s) of formulas (I) and/or (II), in a temperature range of 25° to 30° C. and, if desired, separating the product(s) formed from the fermentation broth, then isolating it in the lactone form of formula (I) and, if desired, purifying the same.

5 Claims, 1 Drawing Sheet

MICROBIAL PROCESS FOR PREPARING MEVINOLIN BY A STRAIN OF ASPERGILLUS

The invention relates to a microbial process for preparing mevinolin (β,δ-dihydroxy-7-[1,2,6,7,8,8a-hexahydro-2,6-dimethyl-8-(2-methylbutyryloxy)-naphthalen-1-yl]-heptanoic acid δ-lactone); (4R,6R)-6-(2-[(1S,2S,6R,8S,8aR)-1,2,6,7,8,8a-hexahydro-8-hydroxy-2,6-dimethylnaphthalen-1-yl]ethyl)tetrahydro-4-hydroxy-2H-pyran-one-8-(S)-2-methylbutanoic acid ester) of the formula (I),

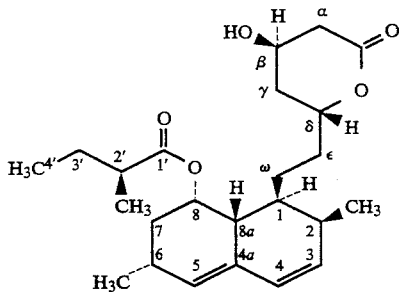

inhibiting the cholesterol biosynthesis in the organism, by applying the fungus *Aspergillus obscurus* n. sp. MV-1.

In the filamentous fungus strains mevinolin is biosynthesized from acetate residues via the polyketide metabolic pathway. The skeleton of the mevinolin molecule is built up from nine acetate moieties while the butyric acid side-chain from two acetate moieties. Mevinolin also contains two methyl groups originating from methionine [R. N. Moore et al.: *J. Am. Chem. Soc.* 107, 3694–3701 (1985)]. Mevinolin was first isolated by A. Endo from the culture of the fungus *Monascus ruber*, in 1979 [*J. Antibiot.* 32,852–854, 1979), thereafter it was produced by fermentation with *Aspergillus terreus* by A. W. Alberts et al. [*Proc. Natl. Acad. Sci. USA*, 77, 3957–3961 (1980)].

Presently mevinolin, possessing highly favourable mode of action, is the most frequently applied agent in therapy for reducing cholesterol levels. Its open hyroxyacid form, formed in the organism, is a potent inhibitor of the 3-hydroxy-3-methyl-glutarylcoenzyme A reductase enzyme, which catalyses the formation of mevalonic acid, an early intermediate of cholesterol biosynthesis. Mevinolin is especifically advantageous because, as a result of its application, biosynthetic intermediates with a toxic steroid skeleton, formed at a later stage of biosynthesis fail to accumulate in the organism.

Mevinolin, as an intracellular enzyme inibitor, reduces intracellular cholesterol levels, and simultaneously increases the number of LDL-receptors at the surface of the cell membrane which remove the LDL-cholsterol circulating in the blood, thereby inducing the lowering of blood plasma cholesterol level.

In the patent literature the following microorganisms were used for the production of mevinolin: *Monascus anka, Monascus purpurous, Monascus ruber, Monascus vitreus, Monasous paxii* (British Patent Specifications Nos. 2,046,737 and 2,049,664), *Aspergillus terreus* (U.S. Pat. No. 4,231,938).

Formation of small amounts of mevinolin was observed also in the fungus cultures of Phoma sp. M 4452, *Doratomyces nanus* IFO 9551 and *Gymnoascus umbrinus* IFO 8450 [A. Endo et al.: *J. Antibiot.* 39, 1609–1610 (1986)].

Several processes were described for isolating mevinolin from fermentation broths by R. L. Monaghan et al. [U.S. Pat. No. 4,319,039]. In one of the processes the fungus cells are filtered from the fermentation broth then mevinolin is extracted from the filtrate with ethyl acetate and from the cells with 80% aqueous methanol. The combined extracts are evaporated, and the residue obtained is submitted to chromatography, first on a silicagel column, applying ethyl acetate-dichloromethane as eluent, then on a Sephadex LH-20 column, using methanol as developing solvent. Purification is continued again on a silicagel column, applying dichloromethane-acetonitrile as eluent, and finally by reversed phase HPLC, to give the pure product. In the other process the extract of the fermentation broth, obtained similarly to the above procedure, is submitted to gel-filtration on a Sephadex LH-20 column and after preliminary filtration on Waters Bondapack $C_{18}$/Porasil B, the hydroxyacid and the lactone form of mevinolin are obtained and separated on a Waters $\mu C_{18}$ column. Both isolation processes consist of two extraction steps, furthermore of four or three chromatographic steps which are too complicated and expensive processes to permit industrial realization.

A preparative analytical process was also developed for the assay of mevinolin and compounds of related structure. Mevinolin is extracted from the fermentation broth by the absorption resin XAD-2 then is eluted with a mixture of isopropanol-ethyl acetate-dichloromethane and the biological activity of the eluate is assayed.

T. Kazuhiko et al. (British Patent Specification No. 2,049,664) used the extraction process described by R. L. Monaghan to isolate mevinolin from the filtrate and cells of Monascus strains. The combined extracts are evaporated and the resulting crude product is purified by three subsequent chromatographic steps on silicagel columns, using the following developing solvents: dichloromethane-ethyl acetate in the first, n-hexane-acetone in the second and finally benzene-ethyl acetate in the third column, thereafter mevinolin is crystallized. This process is unsuitable for industrial production.

A. Endo (British Patent Specification No. 2,046,737) extracted mevinolin from the culture filtrate of *Monascus ruber* by ethyl acetate. The ethyl acetate extract is evaporated and the residue is dissolved in benzene. The benzene solution is first washed with a 5% sodium hydrogen carbonate solution, then it is stirred with a 0.2N sodium hydroxide solution as long as mevinolin is removed from the benzene phase as an open hydroxy acid sodium salt. The aqueous phase is then acidified and extracted with ethyl acetate. Mevinolin is obtained by evaporation of the ethyl acetate extract and crystellized in lactone form from aqueus acetone. The process has the advantage of being devoid of chromatographic steps, but has the disadvantage of having a large number of extraction steps with high solvent requirement. The process omits the isolation of mevinolin bound to the cell mass.

Our investigations were focused on finding a microorganism which would produce mevinolin at higher concentrations and at more advantageous conditions than those known from former patent specifications. During the screening, covering about 20,000 fungus strains a microorganism was selected which was able to biosynthesize mevinolin in a shorter time and at higher levels than the known strains. According to the results of our taxonomic studies this strain proved to be the member of a new species belonging to the genus Aspergillus and we designated it with the "obscurus" specific epithet. Based on these studies the isolated new imperfect fungus strain has been considered by us as the holotype strain of *Aspergillus obscurus* n. sp., numbered as MV-1 and deposited on Apr. 3, 1992 at the International Depository Authority National Collection of Agricultural and Industrial Microorganisms, Budapest, Hungary under the number NCAIM(P)F 001189—, as established under the Budapest Treaty on the International Recognition of the Deposit of Microorganisms for the Purposes of Patent Procedure. The new species is able to produce mevinolin, mostly in the open hydroxyacid form, in very high concentrations under suitable fermentation conditions. This new species biosynthesizes beside the main product only very small quantities of compounds with related structure ($\beta,\delta$-dihydroxy-7-[1,2,6,7,8,8a-hexahydro-2,6-dimethyl-8-(2-methylbutyryloxy)-naphthalen-1-yl]-heptanoic acid methyl ester; 4,5a-dihydromevinolin) thus it is highly suitable for the industrial production of mevinolin.

BRIEF DESCRIPTION OF THE DRAWINGS

FIG. 1/*b*. Microscopic picture of the conidium-carrying heads of *Aspergillus obscurus* n.sp. MV-1.

The taxonomic features of the cultures of this new species or their colonies compared to the main diagnostic patterns of the known Aspergillus species are summarized as follows.

Figure 1A:
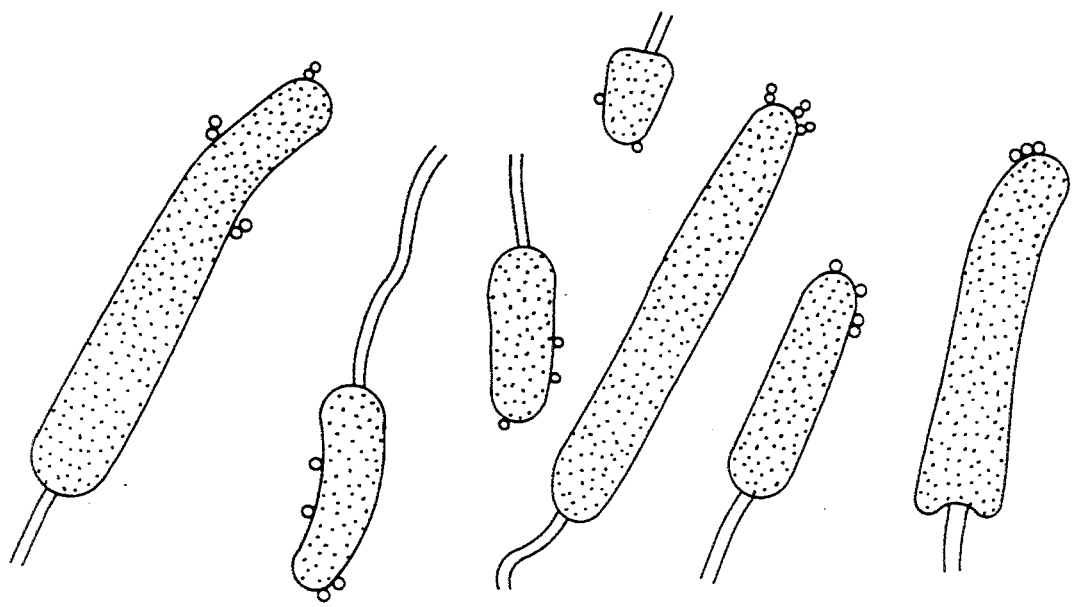
FIG. 1/*a*. Microscopic picture of the conidium-carrying heads of *Aspergillus terreus* ATCC 25042.

The name *Aspergillus obscurus* n. sp. refers to the fact that cultures of the species or their colonies produce a brownish-black mycelial tissue and black soluble pigment on various synthetic and complex media (Tables 1 and 2). Characteristic patterns: At the widening, short, club-like vesicles of the colourless, mostly linear conidiophores there are two rows of phialides. At the head of these secondary phialides the conidia formed are spherical or ovoid, their surface is smooth, with a diameter of 2.0 μm (±0.4 μm). The colour of the mature conidia bearing aerial mycelium is light brown. The conidia-carying conidiophores are dark, club-like (40–60 μm wide) formations, short ($\leq$60–100 μm) and not cylindrical (FIGS. 1/*a* and 1/*b*). FIG. 1/*a* shows the microscopic picture of the conidium-carrying heads of the *Aspergillus terreus* ATCC 20542 strain while FIG. 1/*b* that of the new *Aspergillus obscurus* n. sp. MV-1 strain.

TABLE 1

Cultural, macromorphological comparison of *Aspergillus obscurus* n. sp. strain MV-1 with *Aspergillus terreus* ATCC 20542, biosyntesizing mevinolin, on glycerol-asparagine-agar and glycerol-tyrosine-asparagine media

| Medium | *Aspergillus obscurus* n. sp. MV-1 | *Aspergillus terreus* ATCC 20542 |
|---|---|---|
| Glycerol--asparagine--agar | Aerial mycelium: powder-like median maturity*, light-brown Substrate mycelium: mature, dark brown turning black Soluble pigment: none | Aerial mycelium: mature*, powder-like, brown Substrate mycelium: colourless, then light brownish yellow Soluble pigment: none |
| Glycerol--tyrosine--asparagine--agar | Aerial mycelium: slightly mature sporadically powder-like, brown Substrate mycelium: mature, black Soluble pigment: black | Aerial mycelium: cotton like, reddish-brown, powder like Substrate mycelium: mature, brown Soluble pigment: none |

*"mature" (x5) = strongly developed; "median maturity" (x1) = moderately growing.

TABLE 2

Comparison of strains of *Aspergillus obscurus* n. sp. MV-1 and *Aspergillus terreus* ATCC 20542 according to the colour of the substrate mycelium and soluble pigment on synthetic agar, in the presence of various carbon and nitrogen sources

| C and N source | | *Aspergillus obscurus* MV-1 | *Aspergillus terreus* ATCC 20542 |
|---|---|---|---|
| Maltese | M | Black | Colourless |
| | P | Dark brown | None |
| Xylose | M | Black | Light brown |
| | P | Dark brown | Light brownish-yellow |
| Arabinose | M | Dark brown | Colourless |
| | P | Brown | None |
| Glucose | M | Black | Colourless |
| | P | Brown | None |
| Rhamnose | M | Brown | Yellowish-brown |
| | P | None | None |
| Fructose | M | Black | Colourless |
| | P | Dark brown | None |
| Saccharose | M | Black | Colourless |
| | P | Dark brown | None |
| Inositol | M | Brown | Light brownish-yellow |
| | P | Brown | None |
| Mannitol | M | Dark brown | Light brown |
| | P | Brown | None |
| Raffinose | M | Dark brown | Light brownish-yellow |
| | P | Brown | None |
| Sodium citrate | M | Dark brown-black | Light brown |
| | P | Dark brown | None |
| Ammonium chloride | M | Dark brown-black | Light brown |
| | P | Dark brown | None |
| Calcium nitrate. | M | Dark brown-black | Light brown |
| | P | Dark brown | None |

M = colour of substrate mycelium
P = colour of soluble pigment

Cultural characteristics: Dark brownish black pigmentation is the predominant feature of cultures of strain MV-1 (Tables 1 and 2).

The tables distinctly confirm the highly intense, dark brown and black pigmentation of the substrate mycelium of strain MV-1, this pigment is able to diffuse, in most cases penetrates the medium, too. This pattern is not typical for *Aspergillus terreus* ATCC 20542 where darkish brown pigmentation is solely produced in the substrate mycelium in the presence of tyrosine.

Physiological properties: Aspergillus strains have usually a rather broad spectrum of carbon source utilization. This is also true for strain MV-1 which shows good growth on raffinose, inositol, saccharose, fructose, glucose and maltose. From the nitrogen sources ammonium salts and nitrates are equally well utilized by strain MV-1.

Taxonomy: Though in the MV-1 strain the colour of the aerial mycelium, rich in conidia, is similar to that of *Aspergillus ustus, Aspergillus flavipes* and *Aspergillus terreus* species groups, it can be sharply differentiated from their members.

Figure 1B:
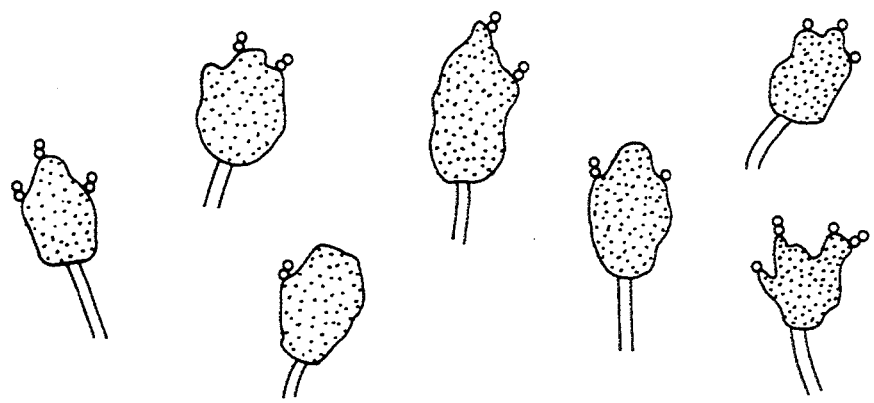

From the last two species groups it can be differentiated first of all on the basis of conidiophores carrying conidia, in *Aspergillus obscurus* n. sp. MV-1 they are not closed or irregularly cylindrical (FIG. 1b). From *Aspergillus ustus* the strain MV-1 differs in its conidia which are smooth and not spiny, furthermore its mature conidiophores are not cylindrical.

Comparing *Aspergillus obscurus* n. sp. MV-1 and *Aspergillus terreus* ATCC 20542 in a parallel test, the strain MV-1 proved to be highly benomil-sensitive (10 μg/ml) compared to the poor sensitivity of the ATCC 20542 strain (50 μg/ml). Furthermore, *Aspergillus terreus* ATCC 20542 shows vigorous growth on galactose, xylose and lactose while strain MV-1 fails to utilize galactose or lactose and only slightly utilizes xylose. There are similar differences in sodium gluconate, sodium salicylate and sodium benzoate utilization, too. *Aspergillus terreus* ATCC 20542 exhibits more or less good growth on these substrates while *Aspergillus obscurus* n. sp. MV-1 very slight or poor growth.

Based on the above presented criteria, the holotype strain MV-1 of *Aspergillus obscurus* may clearly differentiated from the members of the large group of brown Aspergillus spp.

At identifying taxonomically our Aspergillus MV-1 strain we used for comparisons also the Aspergillus species descriptions and redescriptions published by different authors, as follows: Fassatiova, O.: Plisne a vlaknité honby v technické mikrobiologii. Praha, SNTL. Naklad. Techn. Literatury. 1979. and Raper, K. B., Fennell, D.: The genus Aspergillus. Williams and Wilkins Co., Baltimore. 1965.; Subramanian, C. V.: The perfect state of Aspergillus. *Current Science* 41, 753-761 (1972).

In the course of our experiments a new, economic process was developed for isolating mevinolin from fermentation broths. In the fermentation broth a major part of mevinolin is present in the open hydroxyacid form (β,δ-dihydroxy-7-[1,2,6,7,8,8a-hexahydro-2,6-dimethyl-8-(2-methylbutyryloxy)-naphthalen-1-yl]-heptanoic acid) as a salt and only a minor part is present in the lactone form. After concluding the fermentation the product bound to the fungus mass is removed by the addition of 25% ammonium hydroxide stirring and filtering of the alkaline broth. The hydroxyacid form of mevinolin can be isolated from the filtrate by an anion-exchange resin and simultaneously selectively separated from other neutral or basic constituents of the culture filtrate. The product bound to the anion-exchange resin is eluted with a mixture of acetic acid-water-acetone and transformed to mevinolin-lactone with acid and/or heat treatment.

Based on the above, the invention relates to a new process for preparing β,δ-dihydroxy-7-[1,2,6,7,8,8a-hexahydro-2,6-dimethyl-(2-methylbutyryloxy)-naphthalen-1-yl]-heptanoic acid δ-lactone of formula (I) and β,δ-dihydroxy-7-[1,2,6,7,8,8a-hexahydro-2,6-dimethyl-8-(2-methylbutyryloxy)-naphthalen-1-yl]-heptanoic acid of formula (II),

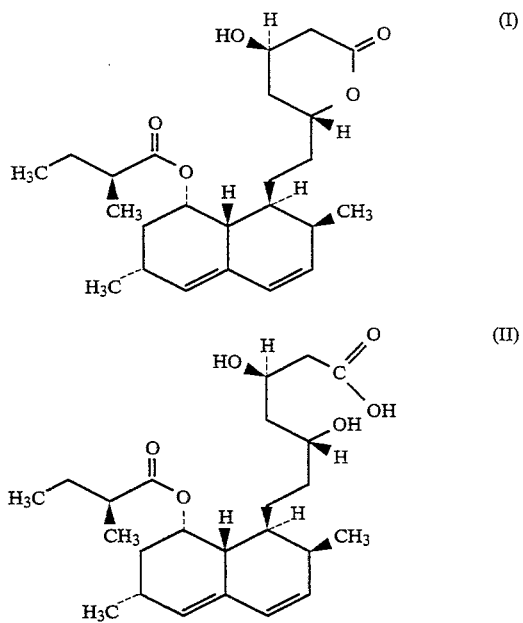

by the aerobic fermentation of the submerged culture of an imperfect fungus strain, biosynthesizing the above compounds in a nutrient medium containing utilizable carbon and nitrogen sources as well as mineral salts, and by isolating the product of formula (I), which comprises cultivating a strain of the new *Aspergillus obscurus* fungus species producing te above compound(s) of formulas (I) and/or (II), preferably the holotype *Aspergillus obscurus* n. sp. MV-1, deposited at the National Collection of Agricultural and Industrial Microorganisms, Budapest, Hungary under the number NCAIM(P)F 001189, in a temperature range of 25° to 30° C. and, if desired, separating the product(s) formed from the fermentation broth, then isolating it in the lactone form of formula (I) and, if desired, purifying the same.

According to a preferred embodiment of the present invention mevinolin is produced with the *Aspergillus obscurus* n. sp. MV-1 strain. The selected strain is highly advantageous due to its fast growth. It is a favourable feature that the strain can utilize glucose, saccharose, maltose, sorbose, fructose, malt extract, molasses, cornmeal, glycerol and water-soluble starch as carbon sources and yeast extract, peptone, bouillon, corn steep liquor, casein, sodium nitrate, ammonium sulfate further soy oil, soymeal and fishmeal as nitrogen sources.

Mineral salts, e.g. magnesium chloride, potassium dihydrogen phosphate, sodium chloride, trace elements (copper, manganese, iron salts), vitamins and antifoam agents can be added to the media serving for the production of mevinolin in addition to the above carbon and nitrogen sources.

According to a preferred embodiment of the process according to the invention a growth medium is inoculated with a filtered spore suspension, prepared from the agar slant culture of *Aspergillus obscurus* n. sp. MV-1, deposited at the National Collection of Agricultural and Industrial Microorganisms, Budapest, Hungary under the number NCAIM(P)F 001189, then the inoculum is incubated for 3 days at 25° to 30° C., preferably at 28° C., thereafter the production medium is inoculated with 10% of this inoculum and incubated at 25° to 30° C., preferably at 25° C., for 5-7 days. During the fermentation the pH is maintained in the range of 3.5 and 6.5, preferably at 6.0. Fermentation is performed under aerobic conditions, at an aeration rate of 400 liter/hour during the growth phase (0–20 hours) and stirring at 400 r.p.m. After 20 hours stirring is increased to 600 r.p.m. with unchanged aeration rate.

During fermentation the active ingredient content of the fermentation broth is monitored by high pressure liquid chromatography and fermentation is stopped at the peak concentration. The broth samples are diluted 2.5 fold with acetonitrile, centrifuged and the supernatants are used for the high pressure liquid chromatographic assay (apparatus: LKB isocratic system; column: Nucleosil $C_{18}$ 5 $\mu$m (BST); column size: first column—4×20 mm, analytical column—4×250 mm; temperature 60° C.; assay at 238 nm; eluent: mixture of 471.6 g of acetonitrile, 400 g of water, and 0.39 of 85% phosphoric acid; flow rate: 1.0 ml/min; injection volume: 10 $\mu$l). Retention times: mevinolin lactone form 9.65±0.05 minutes and mevinolin hydroxyacid form ($\beta$,$\delta$-dihydroxy-7-[1,2,6,7,8,8a-hexahydro-2,6-dimethyl-8-(2-methylbutyryloxy)-naphthalen-1-yl]-heptanoic acid) 6.62±0.05 minutes.

The active ingredient can be removed from the fungus cells instead of ammonium hydroxide also with an other base, e.g. 2N sodium hydroxide or aqueous triethylamine solution.

An anion-exchange resin, preferably in two Dowex 1×2 columns, connected in series, is applied for the isolation of the active ingredient from the filtrate. Instead of Dowex 1×2, Dowex 2×4 (OH⁻), Dowex 1×8 (OH⁻) or IRA 401S (OH⁻) can be used, too. Instead of applying a column the resin can be poured also directly into the broth which can be easily separated from the fungus cells, but this requires an about 20% excess of the resin.

The product bound by the column is eluted with a mixture of acetic acid-water-acetone. The fractions containing the product are combined and the acetone is evaporated. The resulting aqueous concentrate is acidified with 15% sulfuric acid to pH 1.5 and left to stand at room temperature for about 12 hours. During this period the lactone is formed which is monitored by thin-layer chromatography. Then the solution is extracted with ethyl acetate, the ethyl acetate layer is washed with 10% sodium hydrogen carbonate, dried over sodium sulfate and evaporated at reduced pressure. The evaporation residue is decolourized with active carbon in acetone solution and recrystallized from ethanol.

According to a further preferred embodiment of the present invention the feature of the *Aspergillus obscurus* strain that in acid medium (e.g., at pH 2) the product is completely bound to the fungus cells, is exploited for the isolation procedure. In this way, after filtering the mycelium, the filtrate is practically free from the product and its further processing becomes unnecessary. The product is removed from the cells preferably with acetone and the acetone extract is evaporated at reduced pressure. If in the residue there is still any mevinolin in the hydroxyacid form detectable by thin-layer chromatography it is cyclized by refluxing in toluene solution. The crude product obtained can be purified by silica gel column chromatography, preferably using Kieselgel 60 as adsorbent and acetone-benzene (15:85), acetone-n-heptane (30:70), acetone-dichloromethane (15:85), ethyl acetate-n-hexane (30:70) or isopropanol-n-hexane (5:95) mixtures as eluents. At columns of medium pressure (1.5 atm) the crude product can preferably be purified by using a mixture of ethyl acetate-n-hexane (50:50). After the column chromatography the fractions containing mevinolin are combined, evaporated at reduced pressure and the residue is crystallized from a $C_{1-4}$ aliphatic alcohol, preferably from ethanol. Mevinolin can be advantageously crystallized from benzene, acetone, ethyl acetate and acetonitrile, too.

The fermentation process performed with the new *Aspergillus obscurus* n. sp. MV-1 holotype strain has the advantage of applying a new microorganism which has the ability to biosynthesize significant amounts of mevinolin. The new isolation procedure, using an anion-exchange resin, has the major advantage of being easily carried out and being inexpensive as only minor volumes of organic solvents are required.

The other isolation procedure has the advantage that after acidifying the broth both the biosynthesized lactone and hydroxyacid forms of mevinolin are practically fully adsorbed by the fungus mycelium, thus after filtering the processing of large volumes of the filtrate can be avoided.

The structures of the isolated products were identified by UV, IR, $^1$H-NMR, $^{13}$C-NMR and mass spectrometry.

The following examples illustrate the invention without limiting the scope claimed.

EXAMPLE 1

A spore suspension is prepared with 5 ml of a 0.9% sodium chloride solution obtained from a 8–10 day old, malt extract-yeast extract agar slant culture of *Aspergillus obscurus* n. sp. MV-1 NCAIM(P)F 001189 and the suspension is used to inoculate 100 ml of sterile MI inoculum medium in a 500 ml Erlenmeyer flask.

| Composition of MI medium: | |
| --- | --- |
| Glucose | 40 g |
| Casein peptone | 5 g |
| Iron(II) sulfate × 7 $H_2O$ | 0.01 g |
| Potassium chloride | 0.05 g |
| Magnesium sulfate × 7 $H_2O$ | 0.5 g |
| Sodium nitrate | 3 g |
| Potassium dihydrogen phosphate | 2 g |
| in 1000 ml of tap water. | |

The pH of the nutritive medium is adjusted to 6.0 before sterilisation and the mixture is sterilized at 121° C. for 25 minutes. The culture is shaken at a rotary shaker (250 r.p.m.; and amplitude: 2.5 cm) for 3 days, then 5 ml portions of this inoculum culture are used to inoculate 500 ml Erlenmeyer flasks each containing 100 ml of MT medium sterilized at 121° C. for 25 minutes.

| Composition of MT medium: | |
| --- | --- |
| Glucose | 50 g |
| Malt extract | 30 g |
| Gistex yeast extract | 20 g |
| Casein peptone | 20 g |
| Potassium dihydrogen phosphate | 2 g |
| Sodium chloride | 10 g |
| in 1000 ml of tap water. | |

The pH of the nutritive medium is adjusted to 5.5 before sterilization and the mixture is sterilized at 121° C. for 25 minutes. The culture is incubated on a rotary shaker (250 r.p.m.; and amplitude: 2.5 cm) at 25° C. for 5–7 days. The active ingredient content of the fermentation broth is monitored by high-pressure liquid chromatography. The fermentation is continued for 144 hours then mevinolin is isolated from the broth.

After finishing the fermentation 1 liter of the fermentation broth which contained 400 mg/liter mevinolin (both in hydroxy acid form and in lactone form) is acidified to pH 2.0 with 15% sulfuric acid and after two hours the mixture is filtered on a filter cloth. The filtrate, practically free from any active ingredient (10–15 μg/ml), is discarded. The fungus mycelium (about 80 g) is stirred with 200 ml of acetone for 30 minutes then the cell suspension is filtered. This procedure is repeated twice. The combined acetone extracts are dried over anhydrous sodium sulfate and evaporated at reduced pressure. The evaporation residue (about. 4.5 g) is dissolved in 50 ml of toluene and the solution is submitted to analysis by high pressure liquid chromatography. If during the acidification of the fermentation broth the obtained β,δ-hydroxy-7-[1,2,6,7,8,8a-hexahydro-2,6-dimethyl-8-(2-methylbutyryloxy)-naphthalen-1-yl]-heptanoic acid failed to be fully transformed into the lactone, the toluene solution is refluxed for one hour, then the conversion is again controlled. Thereafter the insoluble particles are filtered off from the toluene solution and the toluene layer is washed with 20 ml of 5% sodium hydrogene carbonate and with 20 ml of water, then it is dried over anhydrous sodium sulfate and evaporated at reduced pressure, yielding 1.5–2.0 g of an oily crude product.

The crude product is submitted to chromatography on a column prepared from 20 g of Kieselgel 60 (particle size 0.063–0.2 mm) adsorbent (height: 20 cm, diameter: 1.6 cm). During the preparation of the column the adsorbent is suspended in a mixture of acetone-dichloromethane (15:85). The crude product is applied to the column in a mixture with equal amount of the adsorbent Kieselgel 60 suspended in 10 ml of a mixture of acetone-dichloromethane (15:85). Then the column is eluted with 100 ml of a mixture of acetone-dichloromethane (15:85). 10 ml fractions are collected and monitored by thin-layer chromatography (adsorbent: Kieselgel 60 F$_{254}$ DC Alufoil; developing solvent: acetone-hexane (40:60); R$_f$ of mevinolin: 0.5). Mevinolin is present in fractions 6 to 10 which are evaporated at reduced pressure, yielding 360 g of a solid yellowish-white evaporation residue which is recrystallized from benzene (about. 3 ml). The crystalls formed are filtered on a G-4 glass filter, washed with 5 ml of hexane, dried at reduced pressure and room temperature, yielding 255 mg of chromatographically pure mevinolin. m.p.: 160°–162° C. Evaporating the crystallization mother liquor and recrystallizing the evaporation residue from benzene, a further 25 mg portion of mevinolin is obtained in the same quality as that of the 1st generation. Characteristic spectroscopic data of the mevinolin obtained:

UV spectrum (methanol, 10 μg/ml):
λ$_{max}$ 231, 239, 247 nm
E$_1$ $_{cm}$$^{1\%}$ 530, 620, 410
IR spectrum (KBr pellet:)
3545 cm$^{-1}$ μOH
1725 cm$^{-1}$ μC=O
1700 cm$^{-1}$
$^1$H-NMR spectrum (CDCl$_3$, δ$_{TMS}$=0.00 ppm, J/Hz/):
6.00 (1H) d 4-H J$_{3,4}$=9.7
5.79 (1H) dd 3-H J$_{2,3}$=6.1
5.53 (1H) dd 5-H J$_{5,6}$=3.5; J$_{5,8}$=2.8
5.39 (1H) m 8-H
4.61 (1H) m δ-H
4.37 (1H) m β-H
2.74 (1H) dd α-H$_a$ J$_{α-Ha,α-He}$=17.6; J$_{α-Ha, β-H}$=5.0
2.62 (1H) m α-H$_e$ J$_{α-H,β-H}$=3,8; J$_{α-H,δHe}$=1,5
1.11 (3H) d 2-CH$_3$
1.08 (3H) d 2'-CH$_3$
0.90 (3H) d 6-CH$_3$
0.88 (3H) t 4'-CH$_3$
Mass spectrum (EI, 70 eV):
Molecular ion: 404
Characteristic ions: 404 (M+·), 386 (/M-H$_2$O/+·), 302 (/M-C$_4$H$_9$COOH/+·), 284 (/302-H$_2$O/+·), 224, 198, 172, 159, 157, 57.

EXAMPLE 2

9,2 liters of the MT/1 fermentation medium, sterilized at 121° C. for 45 minutes in a laboratory fermentor, are inoculated with 800 ml of the inoculum shake culture prepared as described in Example 1, then incubated at 25° C., aerated with 400 l/h of sterile air and stirred with a flat blade stirrer at 600 r.p.m.

| Composition of the MT/1 nutritive medium: | |
|---|---|
| Maltose | 60 g |
| Malt extract | 30 g |
| Gistex yeast extract | 20 g |
| Casein peptone | 20 g |
| Potassium dihydrogen phosphate | 2 g |
| Sodium chloride | 10 g |
| in 1000 ml of tap water. | |

The pH of the nutritive medium is adjusted to 5.5 before sterilization. Fermentation is continued for 120 to 144 hours then mevinolin is isolated from the fermentation broth. To the 9.5 l fermentation broth containing 850 μg/ml of mevinolin (—by the end of the fermentation mostly in the hydroxyacid form and to a smaller extent in the lactone form—) 300 ml of 25% ammonium hydroxide are added then the mixture is stirred for 3 hours and filtered. The mevinolin content of the filtrate—in hydroxyacid salt form—amounts to 5.56 g (67%). The filtered fungus mycelium is suspended in 5 liter of 3% ammonium hydroxide solution, stirred for 2 hours, then filtered. The mevinolin content of the filtrate—mostly in hydroxyacid salt form—is 2.1 g (26%). The two filtrates are combined and applied to two columns (diameter 3.2 cm, resin-bed height 34 cm), connected in series, filled with 150 g (270 ml) of Dowex 1×2 (OH−) resin each, at a flow rate of 1100 ml/h, finally the resin bed is washed with 1 liter of deionized water. Thereafter the column is eluted with 2 liters of a mixture of acetic acid-water-acetone (5.7:44.3:50)collecting 200 ml fractions. The fractions are monitored by thin-layer chromatography, using Kieselgel 60 F$_{254}$ DC (Merck) alufoil as adsorbent and acetone-n-hexane-acetic acid (40:60:1)as developing solvent. The plates are visualized by phosphomolybdic acid reagent (1.5 g phosphomolybdic acid+40 ml of methanol+40 ml of water+10 ml of cc. sulfuric acid). The open hydroxyacid form of mevinolin has an R$_f$ value of 0.4, while that of mevinolin is 0.6. The fractions containing these two products are combined and their acetone content is evaporated at reduced pressure. Thereafter the mevinolin content of the aqueous phase, mostly in the open hydroxyacid form, is transformed into the lactone by adding to the concentrate 60 ml of 15% sulfuric acid and storing it at room temperature for 12 hours. Lactone formation is monitored by thin-layer chromatography. After the lactone formation is finished the solution is extracted twice with 200 ml of ethyl acetate, the ethyl acetate extracts are combined, washed twice with 100 ml of 10% sodium hydrogen carbonate solution then with 100 ml of water. The ethyl acetate layer is dried over sodium sulfate and evaporated at reduced presure, yielding 17.5 g of a crude product. This is dissolved in 200 ml of acetone and decolourized with 4 g of charcoal. The charcoal is filtered and the ethyl acetate filtrate is evaporated at reduced pressure, yielding 15.7 g of a solid evaporation residue which is recrystallized from 55 ml of ethanol. The crystals formed are filtered on a G-4 filter and washed with 100 ml of n-hexane. The slightly yellowish crystals (9.7 g) are again recrystallized from 30 ml of ethanol. The mevinolin formed is filtered, washed with 50 ml of n-hexane and dried under reduced pressure at room temperature. Yield: 5.71 g (71%) of the chromatographically pure product, m.p. 160°-162° C. (Boetius). The spectroscopic data of the product are identical to those specified in Example 1.

The combined crystallizing mother liquors are evaporated at reduced pressure, giving 8 g of an evaporation residue which is dissolved in 75 ml of ethyl acetate. The solution is washed twice with 10% sodium hydrogen carbonate then with 35 ml of water. The ethyl acetate solution is dried over anhydrous sodium sulfate and evaporated at reduced pressure. The crude product obtained (4.8 g) is submitted to chromatography on a column prepared from 60 g of Kieselgel 60 adsorbent (column diameter 2.3 cm, adsorbent height 25 cm). A mixture of acetone-dichloromethane (15:85) is applied as eluting solvent. On preparing the chromatographic column the adsorbent is suspended in a mixture of acetone-dichloromethane (15:85), and the crude product is applied in a suspension prepared from 2 g of Kieselgel 60 adsorbent and 20 ml of acetone-dichloromethane (15:85). Thereafter the column is eluted with 400 ml of a mixture of acetone-dichloromethane (15:85), collecting 50 ml fractions. The fractions are monitored by thin-layer chromatography, using Kieselgel 60 $F_{254}$ DC (Merck) as adsorbent and a mixture of acetone-n-hexane (40:60) as developing solvent. The $R_f$ value of 4a,5-dihydromevinolin is 0.52. In fraction 3 4a,5-dihydromevinolin, in fractions 4–8 mevinolin are eluted from the column. The fractions containing mevinolin are combined and evaporated at reduced pressure. The evaporation residue (2 g) is recrystallized from 15 ml of ethanol. The crystals formed are filtered on a G-4 filter, washed on the filter with 10 ml of n-hexane and dried at reduced pressure. Yield 0.73 g (9%) of chromatographically pure mevinolin, m.p. 162°-168° C. (Boetius).

EXAMPLE 3

The pH of 1 liter of the fermentation broth prepared according to the procedure of Example 1 is adjusted to 2 with 15% sulfuric acid. The acidic fermentation broth is extracted three times with 250 ml of ethyl acetate, the combined extracts are dried over anhydrous sodium sulfate and evaporated at reduced pressure. The resulting 6 g of evaporation residue is dissolved in 50 ml of toluene and refluxed for 2 hours. The conversion of the hydroxyacid form to the lactone form of mevinolin is monitored by high pressure liquid chromatography according to the procedure specified in Example 1. After completing the lactone formation the toluene solution is washed first with 25 ml of 10% sodium hydrogen carbonate solution then with 25 ml of water, thereafter it is evaporated at reduced pressure, yielding 4.5 g of evaporation residue. This crude product is submitted to chromatography on a column prepared from 300 g of Kieselgel G, at a pressure of 1.5 bar. The eluting solvent used is a mixture of dried ethyl acetate-n-hexan (50:50) (distilled from calcium hydride or phosphorus pentoxide). The product is applied to the chromatographic column in benzene solution (20 ml). Mevinolin is eluted with a mixture of ethyl acetate-n-hexane (50:50). The fractions containing the product are evaporated at reduced pressure and the 400 mg of evaporation residue is recrystallized from 3 ml of ethanol. The crystals formed are filtered on a G-4 filter, washed on the filter with 10 ml of n-hexane and dried at reduced pressure at room temperature. Yield: 280 mg of chromatographically pure mevinolin, m.p. 162°-165° C. (Boetius).

What we claim is:

1. A microbial process for preparing β,δ-dihydroxy-7-[1,2,6,7,8,8a-hexahydro-2,6-dimethyl-8-(2-methyl-butyryloxy)-naphthalen-1-yl]-heptanoic acid δ-lactone of formula (I) and β,δ-dihydroxy-7-[1,2,6,7,8,8a-hexahydro-2,6-dimethyl-8-(2-methyl-butyryloxy)-naphthalen-1-yl]-heptanoic acid of formula (II),

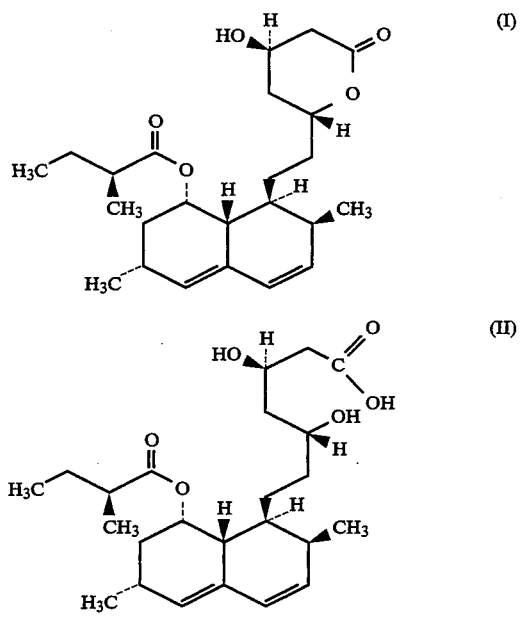

comprising cultivating Aspergillus obscurus NCAIM(P)F 001189 in an aqueous nutrient medium containing assimilable carbon and nitrogen sources at 25° to 30° C., removing the resulting fungal mycelium from said nutrient medium and recovering said compounds of formulas (I) and (II) from said nutrient medium.

2. The process of claim 1, further comprising separating compounds of the formula (I) and formula (II) by anion exchange chromatography.

3. The process of claim 1, wherein the nitrogen source is a compound selected from the group consisting of yeast extract and peptone, and the carbon source is a compound selected from the group consisting of glucose, maltose and saccharose.

4. The process of claim 2 wherein the anion-exchange resin is Dowex ® 1×2 (OH−), Dowex ® 2×4 (OH−), Dowex ® 1×8 (OH−) or IRA ® 401S (OH−).

5. The process of claim 1, wherein the compounds of formula (I) and (II) are recovered from the fungal mycelium after acidifying said aqueous nutrient medium before said fungal mycelium is removed.

* * * * *